US012796923B2

United States Patent
(12) Kim

(10) Patent No.: US 12,796,923 B2
(45) Date of Patent: Nov. 17, 2026

(54) CAMERA FOR DIAGNOSING OPHTHALMIC AND CONTROL METHOD FOR THE SAME

(71) Applicant: CLASSYS INC., Seoul (KR)

(72) Inventor: Yong Han Kim, Anyang-si (KR)

(73) Assignee: CLASSYS INC., Seoul (KR)

(*) Notice: Subject to any disclaimer, the term of this patent is extended or adjusted under 35 U.S.C. 154(b) by 1056 days.

(21) Appl. No.: 17/975,650

(22) Filed: Oct. 28, 2022

(65) Prior Publication Data

US 2024/0138676 A1 May 2, 2024

(51) Int. Cl.
*A61B 3/15* (2006.01)
*A61B 3/00* (2006.01)
*A61B 3/12* (2006.01)

(52) U.S. Cl.
CPC ............ *A61B 3/152* (2013.01); *A61B 3/0025* (2013.01); *A61B 3/0075* (2013.01); *A61B 3/12* (2013.01)

(58) Field of Classification Search
CPC ....... A61B 3/0025; A61B 3/0075; A61B 3/12; A61B 3/1208; A61B 3/152
See application file for complete search history.

(56) References Cited

FOREIGN PATENT DOCUMENTS

| | | | |
|---|---|---|---|
| JP | 2004-290535 | A | 10/2004 |
| JP | 3630887 | B2 | 3/2005 |
| KR | 10-2016-0070233 | A | 6/2016 |
| KR | 10-2017-0044333 | A | 4/2017 |

*Primary Examiner* — Jack Dinh

(74) *Attorney, Agent, or Firm* — Bridgeway IP Law Group, PLLC; Jihun Kim

(57) ABSTRACT

A camera for diagnosing ophthalmic disorders and control method for the same according to an embodiment of the present invention allow not only a skilled ophthalmologist, but also non-specialists, beginners, etc. to easily obtain a fundus image in a preferable form that can be read for diagnosis. In addition, the present invention can stably obtain a fundus image in the preferable form that can be read for diagnosis by a non-specialist or a beginner even in the case of a non-mydriatic method in which the fundus image must be acquired in an instant before the patient blinks by flashing.

9 Claims, 7 Drawing Sheets

CAMERA FOR DIAGNOSING OPHTHALMIC AND CONTROL METHOD FOR THE SAME

BACKGROUND OF THE INVENTION

Field of the Invention

The present invention relates to a camera for diagnosing ophthalmic disorders capable of obtaining a standard form of fundus image used for fundus examination for diagnosing ophthalmic disorders such as cataracts, glaucoma, macular degeneration, and diabetic retinopathy.

Description of the Related Art

Recently, as the elderly population increases, the prevalence of eye diseases that cause blindness, such as cataract, glaucoma, macular degeneration, and diabetic retinopathy, is increasing significantly.

Fundus examination is a test that observes the retina, choroid, and optic nerve papilla (optic disk) only with photographs of the fundus. In the case of eye diseases that cause blindness, such as cataract, glaucoma, macular degeneration, and diabetic retinopathy, it can be diagnosed early with only a basic fundus examination.

Since a conventional fundus camera equipment, which can take fundus images for fundus examination, is quite large and is installed and used in hospitals, the elderly, the disabled, and people living in remote areas cannot even get basic fundus examinations.

In addition, eye disease diagnostic equipment installed in hospitals is difficult to control and move the device if an operator is not an expert and is not widely distributed to health centers or medical institutions in rural areas or remote areas, making it difficult to diagnose and treat early.

In order to solve this problem, a technology related to a portable eye disease diagnosis camera that can be easily carried and moved by an optometrist has been developed.

As such, the technologies related to a portable eye disease diagnosis camera device are disclosing prior arts such as JP2004-290535, JP3630887, KR10-2016-0070233, KR10-2017-0044333.

As the portable eye disease diagnosis camera device as described above was used for field diagnosis without a skilled ophthalmologist, a non-specialist mainly went to the site with a portable eye disease diagnosis camera to acquire fundus images of patients, and sent the acquired fundus images to a remote ophthalmologist or artificial intelligence diagnosis server to enable remote care.

However, while the portable eye disease diagnostic camera as mentioned above is portable and easy to operate, it is difficult to obtain a preferable form of fundus image that can be read by an ophthalmologist. In addition, if a non-specialist obtains a fundus image with a portable eye disease diagnosis camera, it is more difficult to obtain a preferable form of fundus image that can be read. In addition, when diagnosing ophthalmic disorders by artificial intelligence, fundus images taken with the portable eye disease diagnosis cameras as described above have a problem in that the reading rate is poor.

In particular, as opposed to the mydriatic method in which a mydriatic agent is administered to the patient's eye to forcibly dilate the pupil to transmit light, in the case of the non-mydriatic method, which acquires an image of the fundus without administering a mydriatic agent to the eye, the fundus image should be acquired at a momentary moment before the patient blinks due to the flash light.

Therefore, it is more difficult to obtain an easy-to-read or readable fundus image of a preferable form.

SUMMARY OF THE INVENTION

A camera for diagnosing ophthalmic disorders and control method for the same according to an embodiment of the present invention allow not only a skilled ophthalmologist, but also non-specialists, beginners, etc. to easily obtain a fundus image in a preferable form that can be read for diagnosis.

In addition, the camera for diagnosing ophthalmic disorders and control method for the same according to an embodiment of the present invention can stably obtain a fundus image in the preferable form that can be read for diagnosis by a non-specialist or a beginner even in the case of a non-mydriatic method in which the fundus image must be acquired in an instant before the patient blinks by flashing.

A camera for diagnosing ophthalmic disorders according to an embodiment of the present invention comprises: an infrared-light source providing infrared light to a fundus; a white-light source providing white light to the fundus; optical modules for generating an image by the light reflected from the fundus; a display module showing the image generated by the optical modules; and a controller which controls to provide a guide for positioning the infrared fundus image, which is the infrared light-based fundus image, to conform a preset reference fundus image, and to acquire a white-light fundus image, which is the white light based fundus image, when the infrared fundus image is positioned to conform the reference fundus image.

In the camera for diagnosing ophthalmic disorders according an embodiment of the present invention, the controller is configured to provide a position adjustment guide for locating an object corresponding to an optic disk on the infrared fundus image to a position of an optic disk of the reference fundus image, and to control to acquire the white-light fundus image when the object corresponding to the optic disk on the infrared fundus image is moved and located to the position of the optic disk of the reference fundus image.

In the camera for diagnosing ophthalmic disorders according an embodiment of the present invention, the controller is configured to control to display the infrared fundus image in real time on the display module and to display an indicator corresponding to a position of an optic disk on the reference fundus image so that the infrared fundus image can be adjusted to be positioned with reference to the indicator.

The camera for diagnosing ophthalmic disorders according an embodiment of the present invention further comprises an image processor that analyzes the infrared fundus image to detect an object corresponding to an optic disk.

In the camera for diagnosing ophthalmic disorders according an embodiment of the present invention, the controller is configured to control to display a region preset to correspond to an optic disk of the reference fundus image as a target region on the display module, to display the infrared fundus image in real time on the display module, and to display a detection region including an object corresponding to an optic disk detected on the displayed infrared fundus image.

In the camera for diagnosing ophthalmic disorders according an embodiment of the present invention, the controller is configured to control to display movement information to which the detection region is moved so that the detection region on the infrared fundus image matches the target region on the display module.

In the camera for diagnosing ophthalmic disorders according an embodiment of the present invention, the controller is configured to detect whether the detection region moves and matches the target region as the camera moves, and provide feedback when the detection region matches the target region.

The camera for diagnosing ophthalmic disorders according an embodiment of the present invention further comprises a motion sensor detecting movements of the camera, and wherein the controller is configured to control to display movement direction and distance information so that an object corresponding to an optic disk of the infrared fundus image matches a preset position of an optic disk of the reference fundus image on the display module, and wherein, as a result of the detection of the camera movement by the motion sensor, the controller determines whether there is a movement corresponding to the movement direction and distance, and provides feedbacks as the object corresponding to the optic disk on the infrared fundus image approaches the preset position of the optic disk of the reference fundus image.

In the camera for diagnosing ophthalmic disorders according an embodiment of the present invention, the controller monitors the movements of the detection region and provides feedbacks according to the degree of proximity of the detection region to the target region.

A control method for the camera for diagnosing ophthalmic disorders according an embodiment of the present invention comprises: providing infrared light from an infrared-light source to a fundus of a patent's eyeball, generating an infrared fundus image by obtaining a reflected infrared light, and displaying the infrared fundus image on a display module; displaying a guide on the display module so that the infrared fundus image can be conformed a preset reference fundus image; and acquiring a white-light fundus image, which is white light based fundus image, when the infrared fundus image is positioned to conform the reference fundus image.

In the control method according an embodiment of the present invention, the displaying the guide on the display module comprises: displaying a target region preset to a region corresponding to an optic disk of the reference fundus image; and displaying the infrared fundus image in real time on the display module and a detection region including an object corresponding to an optic disk detected on the displayed infrared fundus image.

In the control method according an embodiment of the present invention, the displaying the guide on the display module comprises displaying movement information to which the detection region is moved so that the detection region on the infrared fundus image matches the target region on the display module.

The control method according an embodiment of the present invention further comprises: detecting whether the detection region moves and matches the target region as the camera moves; and providing feedback when the detection region matches the target region.

DESCRIPTION OF THE PREFERRED EMBODIMENTS

The terms used in the present specification will be briefly described, and the present invention will be described in detail.

Terms used in the present invention have selected general terms currently widely used as possible while taking functions in the present invention into consideration, but this may vary depending on the intention or precedent of a technician engaged in the relevant field, the emergence of new technologies, and the like. In addition, in certain cases, there are terms arbitrarily selected by the applicant, and in this case, the meaning of the terms will be described in detail in the description of the corresponding invention. Therefore, the terms used in the present invention should be defined based on the meaning of the term and the overall contents of the present invention, not a simple name of the term.

When a part of the specification is said to "include" a certain element, it means that other elements may be further included rather than excluding other elements unless specifically stated to the contrary. In addition, terms such as "unit" and "module" described in the specification mean units that process at least one function or operation, which may be implemented as hardware or software, or as a combination of hardware and software.

Hereinafter, camera for diagnosing ophthalmic disorders and control method for the same according to embodiments of the present invention will be described in detail with reference to the drawings.

Figure 1:
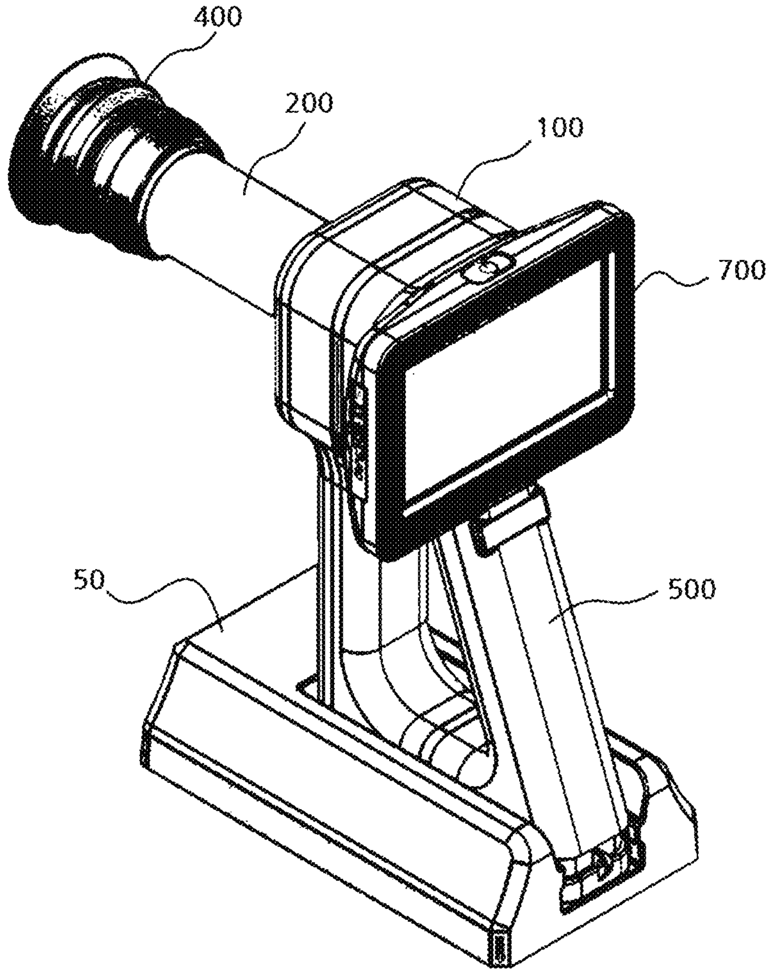
FIG. 1 shows a schematic configuration of a camera for diagnosing ophthalmic disorders according to an embodiment of the present invention.
Figure 2:
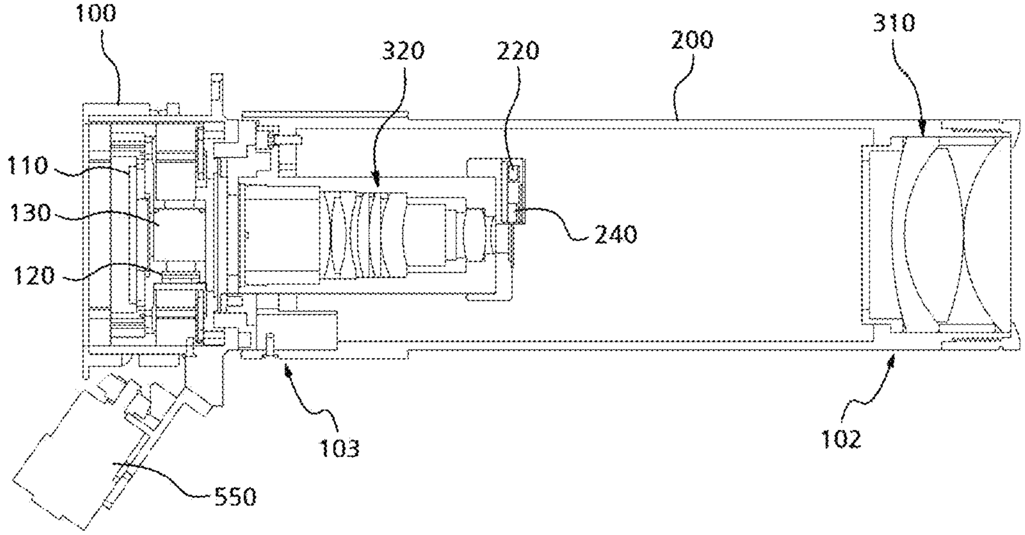
FIG. 2 shows an internal configuration of a camera for diagnosing ophthalmic disorders according to an embodiment of the present invention.
Figure 3:
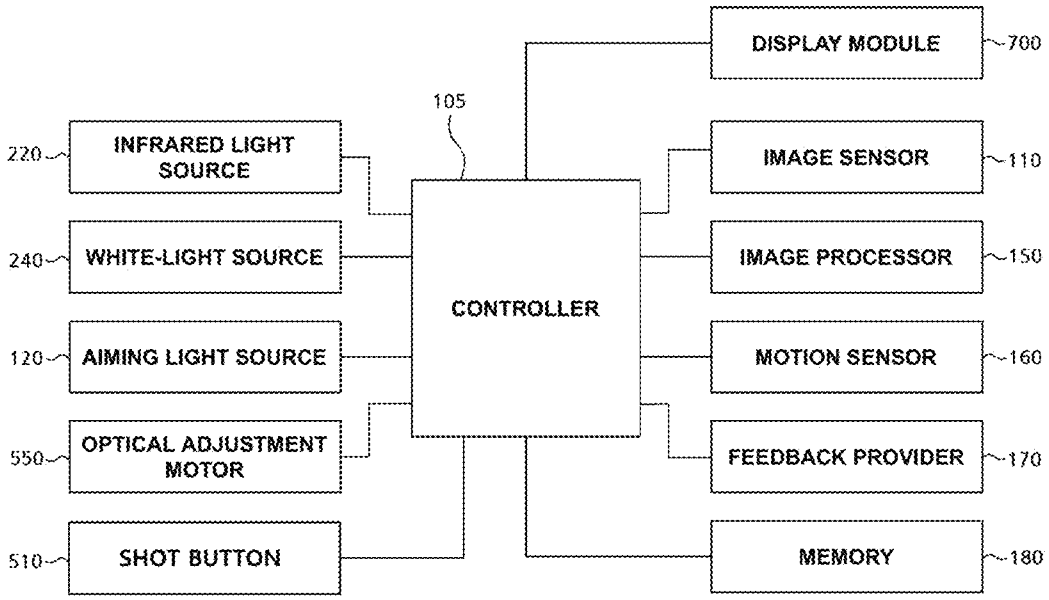
FIG. 3 is a block diagram showing a control system structure of a camera for diagnosing ophthalmic disorders according to an embodiment of the present invention.

A camera for diagnosing ophthalmic disorders according to an embodiment of the present invention will be described with reference to FIGS. 1 to 3. FIG. 1 shows a schematic configuration of a camera for diagnosing ophthalmic disorders according to an embodiment of the present invention, FIG. 2 shows an internal configuration of a camera for diagnosing ophthalmic disorders according to an embodiment of the present invention, and FIG. 3 is a block diagram showing a control system structure of a camera for diagnosing ophthalmic disorders according to an embodiment of the present invention.

The camera for diagnosing ophthalmic disorders according to an embodiment of the present invention may include a camera body 100, an optical tube 200, an eye protector 400, and a display module 700.

The camera body 100 and the optical tube 200 may be equipped with optical modules such as various light sources for acquiring fundus images, a lens assembly for refracting light, and an image sensor for generating fundus images.

The camera body 100 may include components for light processing such as the image sensor, and the optical tube 200 may constitute a path of light and may include components such as various light sources and lens assemblies.

A display module 700 is mounted behind the camera body 100 to display the fundus images generated by the image sensor, so that the operator can easily perform fundus examination.

The distal end of the optical tube 200 may be located in the eye of the patient and may be provided with an eye protector 400 for protecting the eye of the patient. The eye protector 400 may improve the quality of the fundus image by blocking ambient light while protecting the patient's eyes.

The camera for diagnosing ophthalmic disorders according to an embodiment of the present invention may be implemented in a portable type so that the operator may easily use it. For example, as shown in FIG. 1, the camera body 100 may be provided with a handle 500 so that the operator can hold the handle by hand, and a shot button for triggering image capture that can be pressed while the operator holds the handle 500 may be provided on the handle.

In addition, the camera for diagnosing ophthalmic disorders according to an embodiment of the present invention may be implemented to be used wirelessly by its own built-in rechargeable battery without a separate power supply. For example, as shown in FIG. 1, the camera for diagnosing ophthalmic disorders according to an embodiment of the present invention may be detachably coupled to the cradle 50, and as the camera is coupled to the cradle 50, it may be connected to a charging terminal provided in the cradle 50 to be charged.

Therefore, the operator can capture the image of the fundus of the patient's eyeball by holding the handle 500 and placing the eye protector 400 on the patient's eye, and pressing the shot button when appropriate while looking at the image displayed on the display module 700.

Meanwhile, referring to FIG. 2 showing the internal configuration of the camera for diagnosing ophthalmic disorders according to an embodiment of the present invention, the configuration of the optical modules excluding the display module is shown.

FIG. 2 shows the inside of the camera body 100 and the optical tube 200, the distal end 102 of the optical tube 200 is located in the patient's eye, the objective lens assembly 310 may be provided in the distal end 102, and the proximal end 103 of the optical tube 200 may be coupled to the camera body 100.

The optical tube 200 forms an optical path through which light from the light source is reflected from the fundus and proceeds to the image sensor, and an objective lens assembly 310 may be provided on the distal end 102 and an optical lens assembly 320 may be provided on the proximal end 103.

An infrared-light source 220 for irradiating infrared light to the eye and a white-light source 240 for irradiating white light to the eye may be provided inside the optical tube 200.

The objective lens assembly 310 is adjacent to the patient's eyeball and refracts infrared light irradiated from the infrared-light source 220 or white light irradiated from the white-light source 240 to focus on the pupil of the patient's eyeball to reach the entire fundus area through the pupil. And light reflected from the fundus may be transmitted to the optical lens assembly 320. The light passing through the optical lens assembly 320 may reach the image sensor 110 to generate an image.

In this case, the optical adjustment motor 550 may perform focus adjustment on an image by moving a lens constituting the optical lens assembly 320.

Also, inside the camera body 100 or the optical tube 200 may be provided with an guide beam source 120 that generates and transmits guide beam to the patient's eye. The guide beam source 120 generates a specific pattern of guide beam to fix the patient's gaze.

A beam splitter 130 may be provided between the guide beam source 120 and the optical lens assembly 320. The beam splitter 130 allows the guide beam for fixing the gaze to the eyeball to be transmitted to the eyeball through the optical lens assembly 320, and may separate the guide beam and the imaging light (infrared light or white light) by passing the light reflected from the fundus and transmitted through the optical lens assembly 320.

Meanwhile, as shown in FIG. 3, the camera for diagnosing ophthalmic disorders according to an embodiment of the present invention includes control system structure based on the controller 105 capable of controlling all components including an infrared-light source 220, an white-light source 240, an guide beam source 120, an optical adjustment motor 550, a shot button 510, a display module 700, an image sensor 110, a motion sensor 160, a feedback provider 170, and memory 180.

Using the control system centered on the controller as shown in FIG. 3, the camera for diagnosing ophthalmic disorders according to an embodiment of the present invention may acquire an infrared fundus image in real time and may acquire a white-light fundus image fitted to a form of a predetermined reference fundus image using the infrared fundus image.

As described above, the "white-light fundus image fitted to the form of a predetermined reference fundus image" is the fundus image that the camera for diagnosing ophthalmic disorders according to this invention must acquire for final fundus examination. This will be described with reference to FIGS. 4 and 5.

Figure 4:
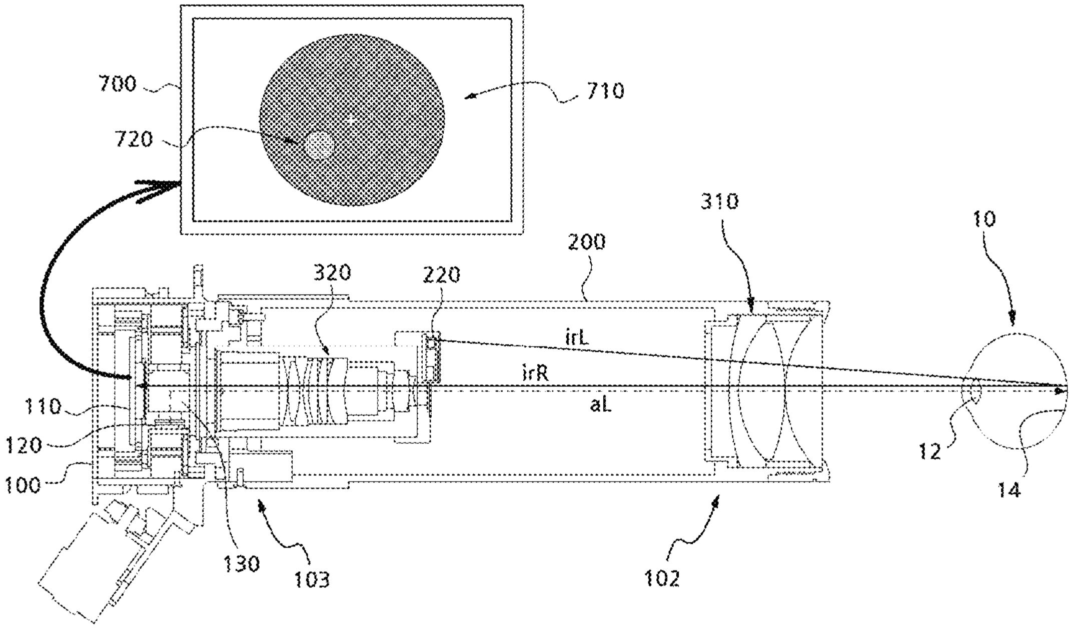
FIG. 4 shows that the camera for diagnosing ophthalmic disorders according to an embodiment of the present invention acquires an infrared fundus image.

By properly positioning the eye protector 400 provided at the end of the optical tube 200 around the patient's eye, the objective lens assembly 310 can maintain an appropriate distance from the patient's eyeball 10, as shown in FIG. 4.

Since the patient's eyeball 10 moves when the gaze is not fixed, the controller controls the guide beam source 120 to transmit the guide beam aL with a specific pattern to the pupil 12 of the eyeball 10. As the patient focuses his/her gaze on the pattern of the guide beam aL, the patient's eyeball 10 may be fixed so as not to move.

In addition, in order to prevent the patient's pupil 12 from constriction, the controller may control the infrared-light source 220 to allow the infrared light irL to be transmitted to the eyeball 10. The infrared light irL may be focused on the pupil 12 of the eyeball 10 through the objective lens assembly 310 to reach the fundus 14.

The reflected light irR reflected by the infrared light from the fundus 10 is transmitted to the objective lens assembly 310 through the pupil 12, and reaches the image sensor 110 through the optical lens assembly 320.

As shown in FIG. 4, the image sensor 110 generates the infrared fundus image 710 based on infrared light from the infrared-light source, and is displayed on the display module 700.

Since the patient does not blink by infrared light, the infrared fundus image 710 may be stably obtained without constriction of the pupil.

However, the infrared fundus image 710 cannot be used for fundus examination because the main parts underlying fundus examination such as an optic disk, macula, and retinal blood vessels of the fundus are not clearly visible in infrared fundus image 710 and the image itself is quite dark overall.

However, since the optic disk appears relatively bright in the infrared fundus image 710, the object 720 corresponding to the optic disk can be specified in the infrared fundus image 710. The object 720 corresponding to the optic disk can be specified by methods such as image analysis by a computer program, for example, a brightness value analysis of pixels, a histogram analysis, etc.

The camera for diagnosing ophthalmic disorders according to an embodiment of the present invention can acquire a white-light fundus image fitted to a predetermined form of a reference fundus image after the position of the object 720 corresponding to the optic disk on the infrared fundus image 710 as described above may be adjusted.

Figure 5:
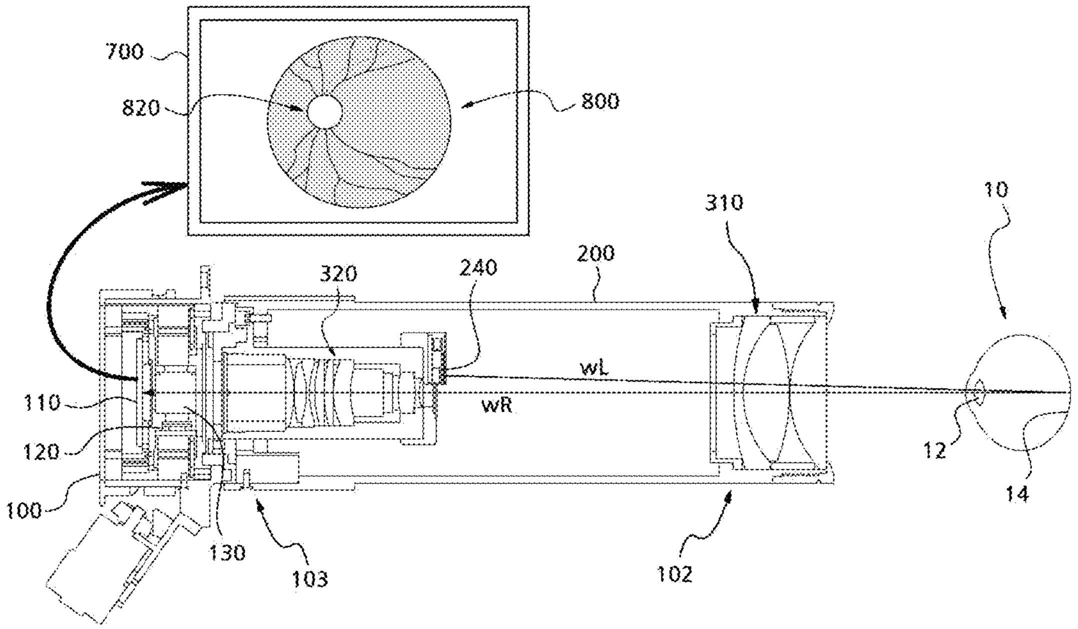
FIG. 5 shows that the camera for diagnosing ophthalmic disorders according to an embodiment of the present invention acquires a white-light fundus image.

As shown in FIG. 4, after the infrared fundus image 710 is generated and the position of the object 720 corresponding to the optic disk is adjusted, automatically or as the operator presses the shot button, as shown in FIG. 5, the controller controls the white-light source 240 to flash white light (wL), and after the white light (wL) reaches the fundus 14 of the eyeball 10 through the objective lens assembly 310, the reflected white-light wR passes through the pupil 12, the objective lens assembly 310, and the optical lens assembly 320 and reaches the image sensor 110 to form an image that is the white-light fundus image.

When the white light WL is transmitted through the pupil 12 of the eyeball 10, the pupil 12 is constricted. Therefore, in a state where the infrared light irL is transmitted through the pupil 12 of the eyeball, when the operator presses the shot button, infrared light is blocked and white light wL is transmitted to the fundus 14 through the pupil 12 of the eyeball in a very short time to obtain reflected white-light wR from the fundus 14. A white-light fundus image can be obtained by a method (i.e., a non-mydriatic method) without forcing the pupil to dilate by administering a mydriatic agent to the eyeball.

As shown in FIG. 5, the image sensor 110 generates a white-light fundus image 800 which is a fundus image based on reflected white-light wR and the white-light fundus image 800 may be displayed on the display module 700.

The white-light fundus image 800 should be taken in a form that can be read by an artificial intelligence diagnostic program or in a form that can be examined by an ophthalmologist, which can be determined based on the position of the optic disk 820.

The controller of the camera for diagnosing ophthalmic disorders according to an embodiment of the present invention may preset the form of the readable fundus image as described above based on the position of the optic disk 820. That is, a fundus image having a form in which the optic disk is located at a predetermined position on the fundus image may be set as a reference fundus image.

However, it is very difficult for the operator to immediately capture the fundus image in the form of the reference fundus image as described above while holding a portable diagnosis camera by hand and placing a eye protector on the patient's eye.

This is because the position of the optic disk on the image can be changed considerably even if the operator moves a little while holding the portable fundus camera by hand.

In addition, in order to check whether the fundus image normally taken with the fundus camera is in the form of a predetermined reference fundus image, a white-light fundus image using white light must be acquired and verified, however, if the fundus image is acquired in a non-mydriatic manner, the pupil constriction immediately due to the short white light flash. Accordingly, It is very difficult to obtain the form of the predetermined reference fundus image with a repetitive method of acquiring, confirming, and re-imaging a white-light fundus image.

According to an embodiment of the present invention, the camera for diagnosing ophthalmic disorders can provide a method of obtaining a white-light fundus image conforming the form of the reference fundus image by obtaining an infrared fundus image in real time using infrared light that does not cause pupil constriction, adjusting the position of the object corresponding to the optic disk on the infrared fundus image, and then flashing white light to capture an image.

FIG. 6 shows an example of moving the camera for diagnosing ophthalmic disorders according to an embodiment of the present invention.

Figure 6A:
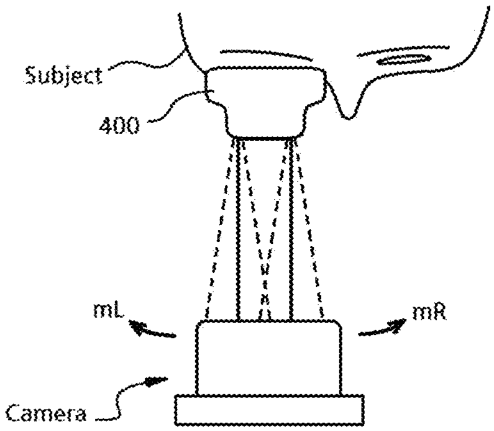
FIGS. 6A-6B show an example of moving the camera to adjust a position of an optic disk on an infrared fundus image to a position of an optic disk on a predetermined reference fundus image in the camera for diagnosing ophthalmic disorders according to an embodiment of the present invention.

As shown in FIG. 6A, the direction of viewing the eye varies as the operator moves (i.e., tilts) the camera to the left (mL) or the right (mR) while the eye protector 400 is fixed around the patient's eyes, so the position of the optic disk on the image is also moved to the left or right.

Figure 6B:
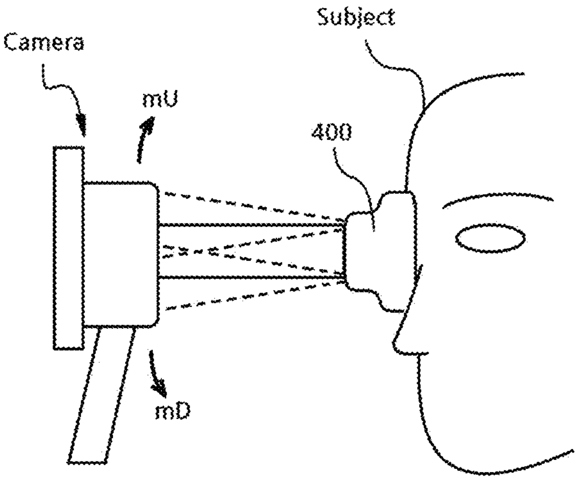

As shown in FIG. 6B, the direction of viewing the eye varies as the operator moves (i.e., tilts) the camera to upward (mU) or downward (mD) while the eye protector 400 is fixed around the patient's eyes, so the position of the optic disk on the image is also moved to upward or downward.

FIG. 7 shows that the camera for diagnosing ophthalmic disorders according to an embodiment of the present invention provides a guide to obtain the infrared fundus image according to the method shown in FIG. 4 and adjust the position of the object corresponding to the optic disk to the predetermined position.

Figure 7A:
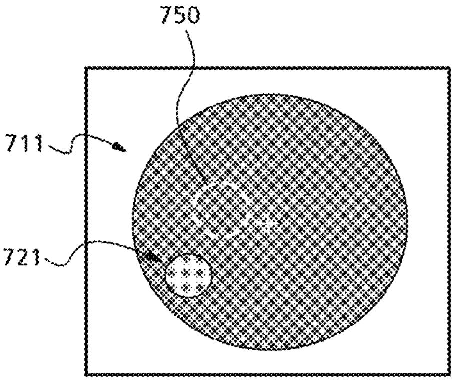
FIGS. 7A-7D show a process in which the camera for diagnosing ophthalmic disorders according to an embodiment of the present invention obtains an infrared fundus image and adjusts the position of an object corresponding to the optic disk to fit a preset position.

FIG. 7A shows the infrared light fundus image 711 captured by the method shown in FIG. 4. As shown in FIG. 7A, the controller may display the predetermined position corresponding to the optic disk on the reference fundus image as an indicator or a target region 750 on the screen of the display module.

Since the indicator or target region 750 is a position corresponding to the optic disk on the reference fundus image, that is, it is predetermined, so the position does not change even if the camera moves.

As shown in FIG. 7A, the infrared fundus image 711 do not show major parts of the fundus, but the part 721 corresponding to the optic disk appears to be specific as an distinct object.

Figure 7B:
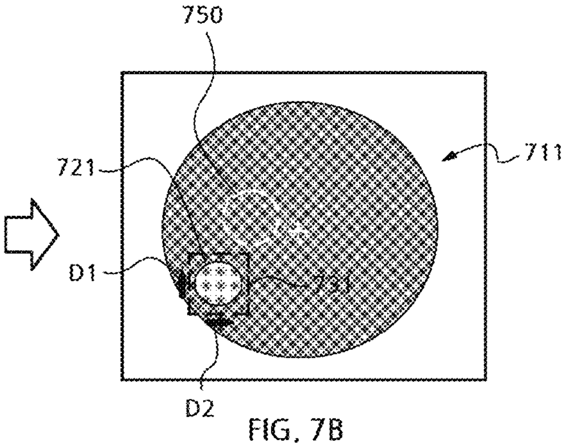

The camera for diagnosing ophthalmic disorders according to an embodiment of the present invention includes an image processor that finds a specific object through image analysis. The image processor may detect an object 721 corresponding to the optic disk by analyzing the infrared fundus image 711 as shown in FIG. 7A, accordingly the controller may display a region corresponding to the detected object 721 as a detection region 731 using the image processor as shown in FIG. 7B.

As shown in FIGS. 6A and 6B, the object corresponding to the optic disk on the infrared fundus image as described above may move in response to the movement of the camera by the operator moves the camera.

Therefore, in order to obtain a fundus image conforming the form of the reference fundus image using the camera, it is necessary for the operator to move the camera to locate the object 721 corresponding to the optic disk at the predetermined position of the optic disk of the reference fundus image.

That is, it is necessary to move the detection region 731 for the object 721 corresponding to the optic disk on the infrared light fundus image 721 and match the target region 750.

The camera for diagnosing ophthalmic disorders according to an embodiment of the present invention displays the infrared fundus image in real time on the display module, an indicator corresponding to the position of the optic disk on the reference fundus image is displayed so that the infrared fundus image can be adjusted to be positioned with reference to the indicator. Accordingly, the operator may move the camera so that the object corresponding to the optic disk on the infrared fundus image can be aimed at the indicator.

The controller may provide, through the display module, a position adjustment guide for aiming at the indicator when the object corresponding to the optic disk on the infrared fundus image is moved in which direction and how much.

As shown in FIG. 7B, in the camera for diagnosing ophthalmic disorders according to another embodiment of the present invention, the controller may provide a position adjustment guide by displaying movement information of the detection region 731 for matching the detection region 731 corresponding to the optic disk 721 on the infrared fundus image 711 to the target region 750 on the display module.

The controller may calculate direction information and/or distance information for moving from the position coordinates of the detection region 731 to the position coordinates of the target region 750 in the coordinate system on the image displayed on the display module as a position adjustment guide, and display the calculated information on the display module.

For example, as shown in FIG. 7B, the movement information of the detection region 731 may include movement direction information D1 and D2 for allowing the detection region 731 to match the target region 750.

As an example of the movement information of the detection region 731, a case in which a marker indicating the direction in which the detection region 731 moves to match the target region 750 is displayed on the display module is shown in FIG. 7B.

Furthermore, the controller may calculate a moving distance for moving from the position coordinate of the detection region 731 to the position coordinate of the target region 750 and display it together with the movement direction information of the detection region 731 on the display module.

For example, the movement distance may be indicated by a number or symbol next to the movement direction arrow marker for the detection region, and the movement distance may be expressed by the size or length of the arrow. For example, the longer the moving distance of the detection region, the longer the length of the arrow may be correspondingly.

According to the movement information of the detection region 731 as described above, the operator can move the detection region 731 by moving the camera as shown in FIGS. 6A and 6B. FIG. 7C shows the state in which the detection region 731 has moved in response to the D1 direction indication.

When the detection region substantially matches the target region, the controller may provide feedback in at least one of visual, auditory, and tactile methods.

Alternatively, the controller may distinguish between horizontal matching and vertical matching of the target region, and provide the feedback whenever any one of the horizontal matching and the vertical matching is completed.

In FIG. 7C, the detection region 732 moves (the object 722 corresponding to the optic disk is moved) to match the horizontal direction of the target region 750, and accordingly, as feedback for the horizontal direction matching, the target region 750 indicates the case where "ok" is marked on the side.

The controller may update the display of the detection region by detecting an object corresponding to the optic disk at every frame or at a predetermined time interval with respect to the infrared fundus image, and movement information for matching the detection region to the target region may be updated.

As shown in FIG. 7C, since the detection region 732 is matched with the horizontal direction of the target region 750, the direction in which the detection region 732 will move can be calculated and displayed again for vertical matching of the target region. FIG. 7C shows that the detection region 732 must move in the D2 direction for vertical matching of the target region.

Figure 7D:
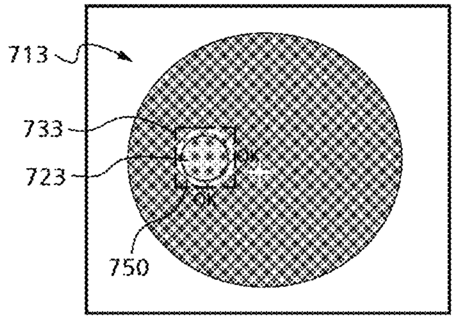
Figure 7C:
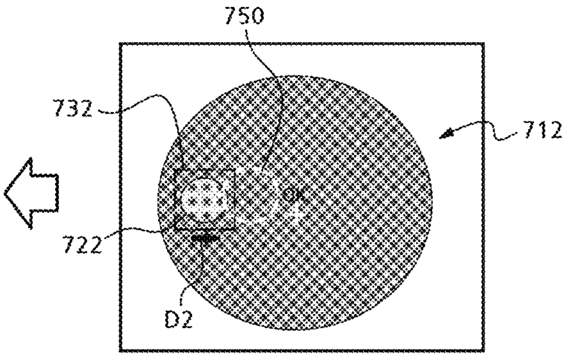

The operator may move the camera so that the detection region 732 moves in the D2 direction, accordingly, as shown in FIG. 7D, the detection region 733 can be completely matched to the target region 750 (That is, the object 723 corresponding to the optic disk on the infrared fundus image 713 may be matched to the target region 750). And according to the matching, the controller may provide feedback. FIG. 7D shows a case in which "ok" is marked under the target region 750 as feedback as the vertical matching is completed.

The feedback as described above may be provided as a visual indication to the display module, alternatively for example, the controller may provide feedback on matching using sound, and may provide feedback on matching using vibration.

The camera for diagnosing ophthalmic disorders according to another embodiment of the present invention may include a motion sensor. The controller may detect the movement of the camera using the motion sensor to monitor the proximity of the detection region to the target region and provide corresponding feedback.

For example, the controller may determine whether there is a movement of the camera corresponding to the movement information of the detection region while detecting the movement of the camera by the motion sensor, and provide feedback according to the degree of proximity of the detection region to the target region.

For example, the feedback may be provided by outputting an interval between beeps gradually shorter as the detection region approaches the target region according to the detection of the motion sensor.

Figures 8A, 8B:
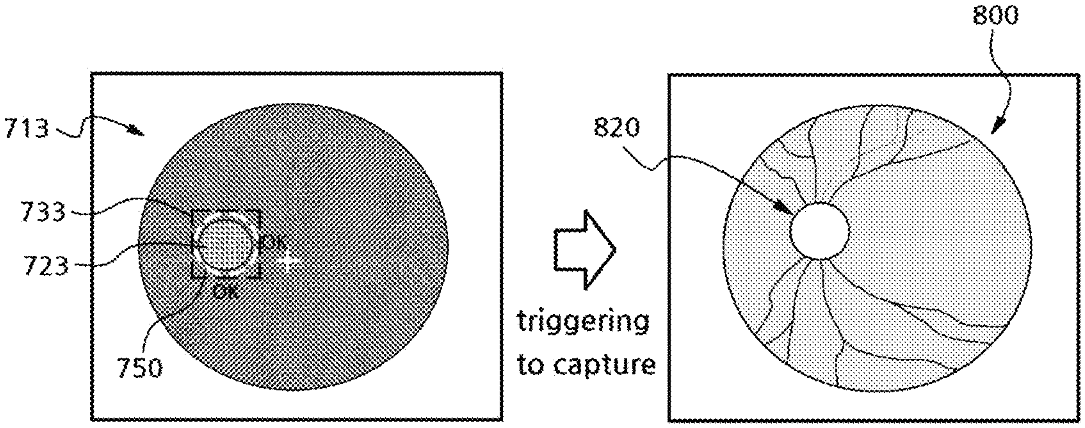
FIGS. 8A-8B show the case where a detection region is matched to a target region through the process shown in FIGS. 7A-7D and the white-light fundus image acquired accordingly.

As shown in FIG. 8A, as the operator moves the camera and moves the detection region 733 (that is, moves the object 723 corresponding to the optic disk on the infrared light fundus image 713) to match the detection region 733 with the target region 750 corresponding to the position of the optic disk of the reference fundus image, automatically or when the operator presses the shot button, the white-light source flashes white light to obtain a white-light fundus image 800 as shown in FIG. 8B.

As shown in FIGS. 7A-7D, in the state that the position is adjusted to the form of the reference fundus image based on the position of the optic disk using the infrared fundus image, the white-light fundus image 800 in which the optic disk 820 is located at a predetermined position as shown in FIG. 8B may be acquired.

The white-light fundus image 800 acquired in this way may correspond to the form of the reference fundus image, that is, a form readable by an artificial intelligence diagnostic program or a form capable of fundus examination by an ophthalmologist.

The controller stores the white-light fundus image obtained as described above in the memory, and may transmit it to an A.I. diagnosis server or an ophthalmologist's PC through a communication network.

Figure 9:
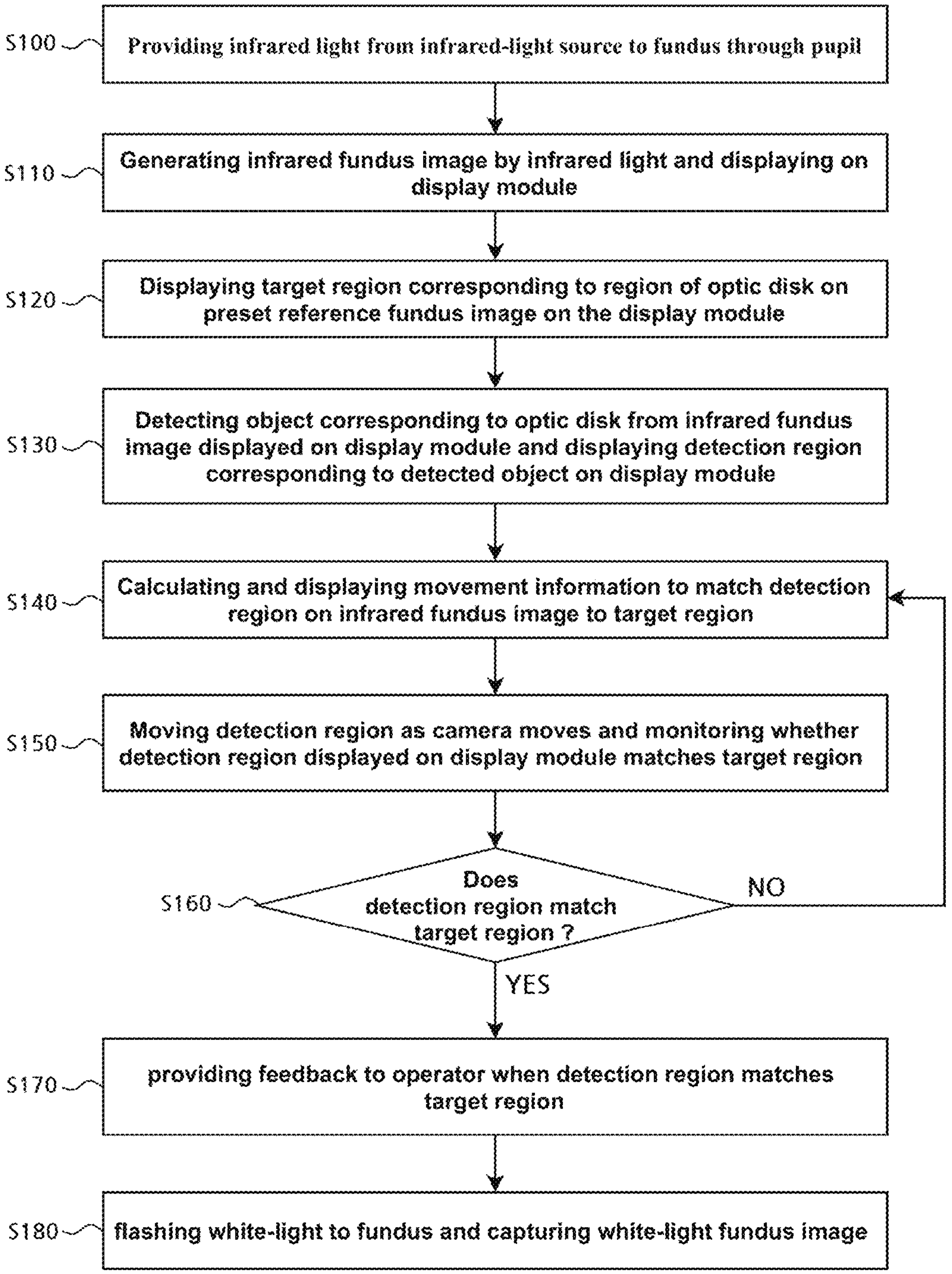
FIG. 9 is a flowchart showing a control method of a camera for diagnosing ophthalmic disorders according to an embodiment of the present invention.

Meanwhile, with reference to the flowchart in FIG. 9, the control method by the controller for the camera for diagnosing ophthalmic disorders according to an embodiment of the present invention will be described. The operation according to the control of the camera for diagnosing ophthalmic disorders according to an embodiment of the present invention has already been substantially described above with reference to FIGS. 4 to 8, and the control method is summarized in the flowchart of FIG. 9.

In a state in which the eye protector of the camera for diagnosing ophthalmic disorders is in close contact with the patient's eye, the controller may control the infrared light to be provided from the infrared-light source so that the infrared light passes through the pupil of the patient's eye and reaches the fundus (S100). Then, an image sensor can generate an infrared fundus image by obtaining the reflected infrared light and display the infrared fundus image on the display module (S110).

The controller may preset a region corresponding to the position of the optic disk on the reference fundus image readable by a diagnosis A.I. or an ophthalmologist and display the preset region as a target region on the screen of the display module (S120).

The controller may detect the optic disk from the infrared fundus image displayed on the display module using the image processor, and display a detection region corresponding to the detected object of the optic disk (S130).

The controller may calculate movement information for matching the detection region on the infrared fundus image to the target region and display the calculated movement information on the display module (S140).

The detection region moves on the display module as the operator moves the camera, the controller may detect whether the detection region displayed on the display module matches the target region (S150).

The controller may detect whether the detection region matches the target region while updating the position of the detection region by detecting the position of the optic disk on the infrared fundus image that changes as the operator moves the camera.

When the detection region matches the target region (S160), the controller may provide feedback according to the target region matching (S170).

Then, by flashing white light, a white-light fundus image conforming to the form of the reference fundus image may be acquired as a final fundus image (S180).

As described above, a camera for diagnosing ophthalmic disorders and control method for the same according to an embodiment of the present invention may allow not only a skilled ophthalmologist, but also non-specialists, beginners, etc. to easily obtain a fundus image in a preferable form that can be read for diagnosis.

In addition, the camera for diagnosing ophthalmic disorders and control method for the same according to an embodiment of the present invention may stably obtain a fundus image in the preferable form that can be read for diagnosis by a non-specialist or a beginner even in the case of a non-mydriatic method in which the fundus image must be acquired in an instant before the patient blinks by flashing.

What is claimed is:

1. A camera for diagnosing ophthalmic disorders comprising:
- an infrared-light source providing infrared light to a fundus;
- a white-light source providing white light to the fundus;
- optical modules for generating an image by the light reflected from the fundus;
- a display module showing the image generated by the optical modules; and
- a controller which controls to provide a guide for positioning the infrared fundus image, which is the infrared light-based fundus image, to conform a preset reference fundus image, and to acquire a white-light fundus image, which is the white light based fundus image, when the infrared fundus image is positioned to conform the reference fundus image.

2. The camera for diagnosing ophthalmic disorders according to claim 1, wherein the controller is configured to provide a position adjustment guide for locating an object corresponding to an optic disk on the infrared fundus image to a position of an optic disk of the reference fundus image, and to control to acquire the white-light fundus image when the object corresponding to the optic disk on the infrared fundus image is moved and located to the position of the optic disk of the reference fundus image.

3. The camera for diagnosing ophthalmic disorders according to claim 1, wherein the controller is configured to control to display the infrared fundus image in real time on the display module and to display an indicator corresponding to a position of an optic disk on the reference fundus image so that the infrared fundus image can be adjusted to be positioned with reference to the indicator.

4. The camera for diagnosing ophthalmic disorders according to claim 1, further comprising an image processor that analyzes the infrared fundus image to detect an object corresponding to an optic disk.

5. The camera for diagnosing ophthalmic disorders according to claim 1, wherein the controller is configured to control to display a region preset to correspond to an optic disk of the reference fundus image as a target region on the display module, to display the infrared fundus image in real time on the display module, and to display a detection region including an object corresponding to an optic disk detected on the displayed infrared fundus image.

6. The camera for diagnosing ophthalmic disorders according to claim 5, wherein the controller is configured to control to display movement information to which the detection region is moved so that the detection region on the infrared fundus image matches the target region on the display module.

7. The camera for diagnosing ophthalmic disorders according to claim 6, wherein the controller monitors the movements of the detection region and provides feedbacks according to the degree of proximity of the detection region to the target region.

8. The camera for diagnosing ophthalmic disorders according to claim 5, wherein the controller is configured to detect whether the detection region moves and matches the target region as the camera moves, and provide feedback when the detection region matches the target region.

9. The camera for diagnosing ophthalmic disorders according to claim 1, further comprising a motion sensor detecting movements of the camera, and wherein the controller is configured to control to display movement direction and distance information so that an object corresponding to an optic disk of the infrared fundus image matches a preset position of an optic disk of the reference fundus image on the display module, and wherein, as a result of the detection of the camera movement by the motion sensor, the controller determines whether there is a movement corresponding to the movement direction and distance, and provides feedbacks as the object corresponding to the optic disk on the infrared fundus image approaches the preset position of the optic disk of the reference fundus image.

* * * * *